(12) United States Patent
Soga et al.

(10) Patent No.: US 8,531,674 B2
(45) Date of Patent: Sep. 10, 2013

(54) MICROSCOPIC TOTAL REFLECTION MEASURING APPARATUS

(75) Inventors: Noriaki Soga, Hachioji (JP); Hiroshi Sugiyama, Hachioji (JP); Takayuki Sera, Hachioji (JP); Jun Koshoubu, Hachioji (JP)

(73) Assignee: JASCO Corporation, Hachioji-shi, Tokyo (JP)

( * ) Notice: Subject to any disclaimer, the term of this patent is extended or adjusted under 35 U.S.C. 154(b) by 413 days.

(21) Appl. No.: 12/763,311

(22) Filed: Apr. 20, 2010

(65) Prior Publication Data

US 2010/0309455 A1 Dec. 9, 2010

(30) Foreign Application Priority Data

Jun. 4, 2009 (JP) .................................. 2009-135258

(51) Int. Cl.
*G01B 9/02* (2006.01)
*G01J 3/00* (2006.01)
*G01J 5/02* (2006.01)

(52) U.S. Cl.
USPC ........................... 356/450; 356/51; 250/341.1

(58) Field of Classification Search
USPC ................... 356/124, 128–136, 237.1–237.6, 356/300–334, 450, 432, 445–448, 51; 250/341.1; 359/859
See application file for complete search history.

(56) References Cited

U.S. PATENT DOCUMENTS 3,259,012 A 7/1966 Locquin
3,992,112 A * 11/1976 Adrion .......................... 356/432

(Continued)

FOREIGN PATENT DOCUMENTS

| JP | 06-003262 | 1/1994 |
|---|---|---|
| JP | 7-12717 | 1/1995 |
| JP | 11-166889 | 6/1999 |
| WO | 96/27784 | 9/1996 |
| WO | 2007/122414 | 11/2007 |

OTHER PUBLICATIONS

Japanese Abstract for Publication No. 07-012717 published Jan. 17, 1995, nine pages.

(Continued)

*Primary Examiner* — Gregory J Toatley
*Assistant Examiner* — Dominic J Bologna
(74) *Attorney, Agent, or Firm* — Rankin, Hill & Clark LLP

(57) ABSTRACT

An object of the present invention is to provide a total reflection measuring apparatus which, while visually observing a specific minute area of a measurement object, is capable of efficiently obtaining optical data on the basis of the total reflection measurement. A microscopic total reflection measuring apparatus of the present invention comprises a Cassegrain mirror 12 having a Cassegrain primary mirror 16 and a Cassegrain secondary mirror 18, which condenses an incident light beam 30 on a measurement object 20 by making an incident light beam successively reflected by the secondary mirror 18 and the primary mirror 16, and which obtains a reflected light beam 32 from the measurement object 20 by making the reflected light beam 32 successively reflected by the primary mirror 16 and the secondary mirror 18. And, a total reflection prism 14 is arranged below the Cassegrain secondary mirror 18. And the incident light beam includes a visible light beam for visual observation and a measurement light beam for acquisition of analysis information, and present invention comprises a visible light filter which separates at least one of the incident light beam to the total reflection prism and the reflected light beam from the total reflection prism 14 into a total reflection area B and a normal reflection area A, and which removes, from the one of the incident light beam and the reflected light beam, the visible light beam in the total reflection area B.

3 Claims, 3 Drawing Sheets

(56) References Cited

U.S. PATENT DOCUMENTS

| | | | | |
|---|---|---|---|---|
| 4,519,707 | A | * | 5/1985 | Kuffer .......................... 356/326 |
| 4,780,832 | A | * | 10/1988 | Shah ............................ 702/130 |
| 4,922,104 | A | * | 5/1990 | Eguchi et al. ............ 250/339.08 |
| 5,347,364 | A | | 9/1994 | Kawasaki et al. |
| 7,049,597 | B2 | * | 5/2006 | Bodkin ........................ 250/353 |
| 2004/0174523 | A1 | | 9/2004 | Uhl et al. |
| 2009/0108187 | A1 | | 4/2009 | Yokoi |

OTHER PUBLICATIONS

European Search Report for Application No. 10159812 mailed Jun. 15, 2010, six pages.

Patent Abstracts of Japan, Publication No. 06-003262, 7 pages.

Patent Abstracts of Japan, Publication No. 11-166889, 12 pages.

* cited by examiner

MICROSCOPIC TOTAL REFLECTION MEASURING APPARATUS

RELATED APPLICATIONS

This application claims the priority of Japanese Patent Application No. 2009-135258 filed on Jun. 4, 2009, which are incorporated herein by reference.

FIELD OF THE INVENTION

The present invention relates to an improvement of a microscopic total reflection measuring apparatus, and more particularly to an improvement of a mechanism for observing the surface of a measurement object by visible light.

BACKGROUND OF THE INVENTION

A microscope has been widely used to measure physical properties, and the like, of various measurement objects. For example, infrared spectra of a measurement object can be measured by using a microscope, so that components, and the like, of a specific minute area of the measurement object can be measured on the basis of the characteristics of the infrared spectra.

Meanwhile, in order to obtain optical data of the measurement object in this way, it is necessary to collect a light beam reflected from the measurement object or a light beam transmitted through the measurement object.

However, the method of collecting a light beam reflected from or transmitted through a measurement object is extremely difficult to be applied to such as the analysis of the surface of a material of a polymer membrane, a semiconductor, and the like, or the analysis of a material exhibiting very strong light absorption characteristics, such as, for example, a solute in an aqueous solution whose infrared spectra have been difficult to be measured.

Thus, a total reflection measuring method is applied to a measurement object to which the above described general method of measuring a reflected or transmitted light beam is difficult to be applied.

In the total reflection measuring method, an ATR hemispherical prism or an ATR triangle pole prism, which has a larger refractive index $n_1$ than a refractive index $n_2$ of a measurement object, is mounted on the measurement object so as to make a luminous flux having a wavelength $\lambda$ incident on the prism from the outside.

Then, when the incident angle $\theta$ from the prism to the measurement object is set larger than the critical angle $\theta_c$, the incident light beam is totally reflected on the critical surface between the measurement object and the prism, but at the reflection point, a slight part of the luminous flux penetrates into the measurement object. When the penetration depth $d_p$ of the light beam is defined by the depth at which the light intensity is reduced to 1/e, and when the wavelength of the light beam is $\lambda$, the penetration depth $d_p$ is expressed by the following expression 1.

$$d_p = \lambda / [2\pi n_1 \{(\sin^2\theta - (n_2/n_1)^2\}^{1/2}] \quad \text{Expression 1}$$

Therefore, when the light beam is absorbed by the measurement object, the amount of the light beam totally reflected on the critical surface is reduced by the absorbed amount. By analyzing the characteristics of the light beam totally reflected on the critical surface between the measurement object and the prism, it is possible to obtain the optical information from the measurement object, even in the case where the surface of a polymer membrane, a semiconductor, and the like, is analyzed, or where the measurement object exhibits very strong light absorption characteristics.

However, in the case where the conventional total reflection measuring apparatus is applied to a general microscopic measuring apparatus, the surface state of the measurement object cannot be grasped even by visually observing the totally reflected light beam. Thus, it is necessary that, after the measurement area on the measurement object is visually observed by visible light in the state where the prismis retreated from the optical path, the prism is returned to the optical path so as to optically obtain the information. Therefore, the operation is complicated and also there is a limit in the improvement of the measurement accuracy.

Patent literature 1: Japanese published unexamined application No. 07-12717

DISCLOSURE OF THE INVENTION

Problem to be Solved by the Invention

The present invention has been made in view of the above described technical problems. An object of the present invention is to provide a total reflection measuring apparatus which, while visually observing a specific minute area of a measurement object, is capable of efficiently obtaining optical data on the basis of the total reflection measurement.

Means to Solve the Problem

To this end, the total reflection measuring apparatus according to the present invention includes a Cassegrain mirror and a prism.

Further, the Cassegrain mirror has a Cassegrain primary mirror and a Cassegrain secondary mirror, and is configured such that an incident light beam is reflected successively by the secondary mirror and the primary mirror so as to be condensed on a measurement object, and such that the light beam reflected by the measurement object is reflected successively by the primary mirror and the secondary mirror so as to be captured.

Further, the total reflection prism is arranged below the Cassegrain secondary mirror.

Further, the total reflection measuring apparatus according to the present invention is featured in that a visible light beam for visual observation and a measurement light beam for acquisition of analysis information are included in the incident light beam, and is featured by further including a filter which separates at least one of the incident light beam to the total reflection prism and the reflected light beam from the total reflection prism into a total reflection area and a normal reflection area, and which removes the visible light beam in the total reflection area from the one of the incident and reflected light beams.

Further, it is preferred in the total reflection measuring apparatus that the filter is stuck to the total reflection prism.

Further, it is preferred in the total reflection measuring apparatus that the total reflection prism is hemispherical and that the filter is formed concentrically with respect to the total reflection prism.

Further, it is preferred in the total reflection measuring apparatus that the measurement light beam for acquisition of analysis information is an infrared interference light beam.

In this way, the microscopic total reflection measuring apparatus according to the present invention uses, as the incident light beam, the light beam formed by mixing the visible light beam and the measurement light beam, and irradiates the incident light beam onto the prism by using the Cassegrain mirror. Further, the microscopic total reflection measuring apparatus according to the present invention selects the observation light beam in the normal reflection area from the reflected light beam so as to use the selected light beam for visual observation, and uses the measurement light beam in the total reflection area for component analysis, and the like.

Effect of the Invention

As described above, in the microscopic total reflection measuring apparatus according to the present invention, among the reflected light beams emitted from the total reflection prism, the visible light beam in the normal reflection area is used for visual observation, and the light beam in the total reflection area is used for the measurement, such as the analysis. Thus, it is possible to perform the analysis, and the like, on the basis of the totally reflected light beam, while performing the visual observation of the area to be measured.

DESCRIPTION OF REFERENCE NUMBERS 10 microscopic total reflection measuring apparatus
12 Cassegrain mirror
14 prism
20 measurement object
52, 54 filter

BEST MODE FOR CARRYING OUT THE INVENTION

In the following, a preferred embodiment according to the present invention will be described with reference to the accompanying drawings.

Figure 1:
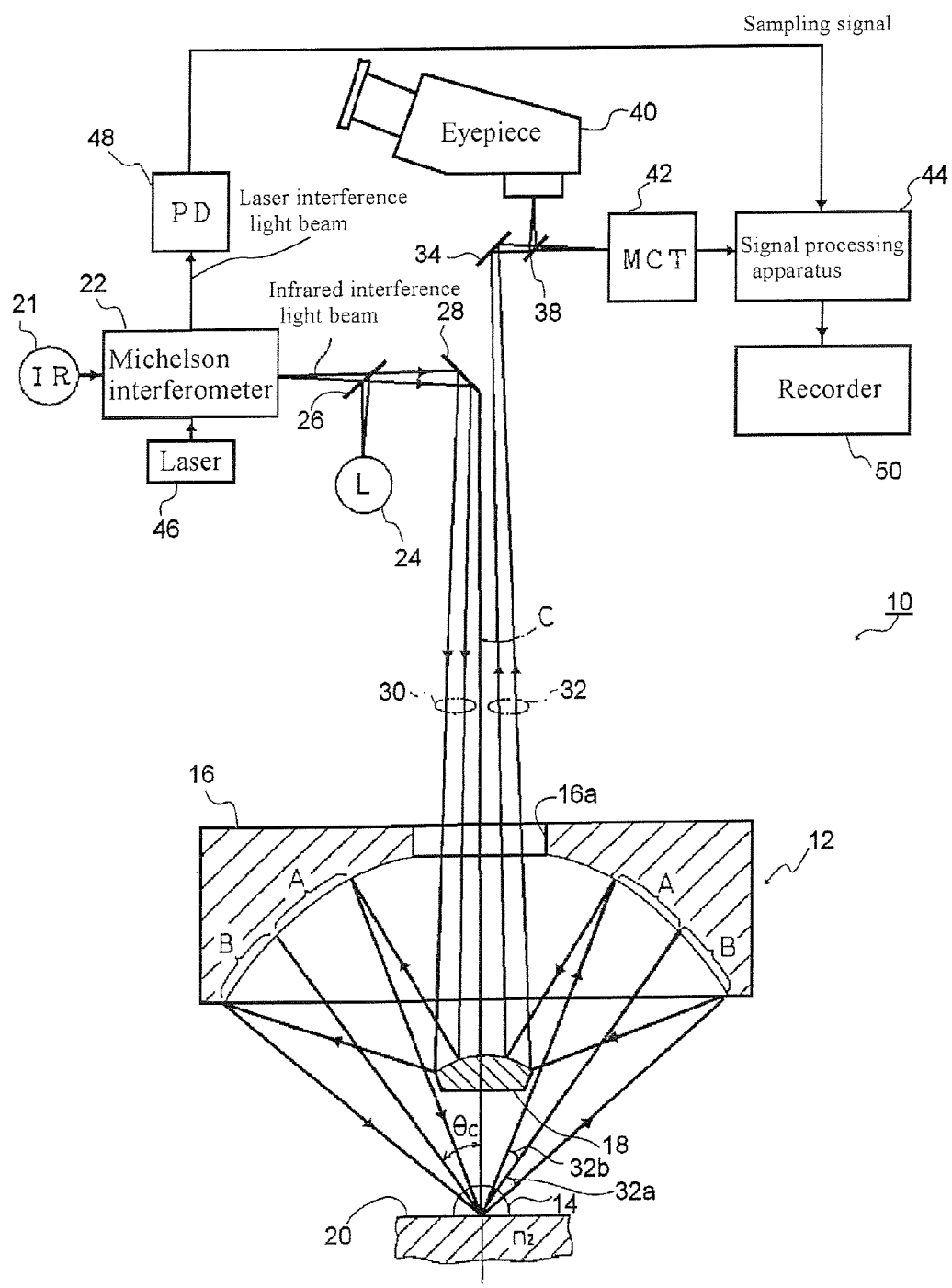
FIG. 1 is a view showing a schematic configuration of a microscopic total reflection measuring apparatus according to an embodiment of the present invention.

FIG. 1 shows a schematic configuration of a microscopic total reflection measuring apparatus according to an embodiment of the present invention.

A microscopic total reflection measuring apparatus 10 shown in FIG. 1 includes a Cassegrain mirror 12 and a hemispherical prism 14.

The Cassegrain mirror 12 is configured such that a Cassegrain primary mirror 16 configured by a concave mirror at the center portion of which a hole 16a is formed, and a Cassegrain secondary mirror 18 configured by a convex mirror whose diameter is smaller than that of the Cassegrain primary mirror 16 are arranged to make the central axes C of the mirrors coincide with each other.

The prism 14 is formed into an approximately hemispherical shape, and can be arranged such that the convex surface of the prism 14 faces the Cassegrain primary mirror 16, such that the central axis of the convex surface of the prism 14 coincides with the central axis C of the Cassegrain mirror 12, and such that the center point of the convex surface of the prism 14 coincides with the position at which the light beam is converged by the Cassegrain mirror 12.

Further, in the case where a measurement point on a measurement object 20 is observed, an incident light beam 30 is formed in such a manner that an infrared interference light beam (measurement light beam) obtained from an infrared light source 21 and a Michelson interferometer 22, and a visible light beam (observation light beam) obtained from a visible light source 24 are mixed with each other by a half mirror 26, so as to be reflected by a fixed mirror 28. The formed incident light beam 30 is made incident onto the prism 14 via the Cassegrain mirror 12. In the present embodiment, the light beam reflected by the measurement object 20 is reflected by the Cassegrain primary mirror 16 and the Cassegrain secondary mirror 18, so as to become an emitted light beam 32. The emitted light beam 32 is reflected by a fixed mirror 34 and is further separated into a visible light beam and an infrared light beam by a separation half mirror 38. The obtained visible light beam is guided to an eyepiece 40.

On the other hand, in the case where the total reflection spectra are measured, the emitted light beam 32 is reflected by the fixed mirror 34, and is separated by the separation half mirror 38 so that the infrared light beam is selected. Then, the intensity of the infrared light beam is detected by an MCT detector 42, and the detected signal is supplied to a signal processing apparatus 44. At that time, a laser light beam emitted from a laser 46 is guided to the Michelson interferometer 22, so that a laser interference light beam is generated. The intensity of the laser interference light beam is detected by a photodiode 48, and the detected signal is supplied, as a sampling signal, to the signal processing apparatus 44. The signal processing apparatus 44 reads the light intensity signal from the MCT detector 42 in synchronization with the sampling signal. Then, the signal processing apparatus 44 acquires infrared absorption spectra by applying known signal processing, such as Fourier transform, to the light intensity signal, and makes the infrared spectra stored in a recorder 50.

Figure 2:
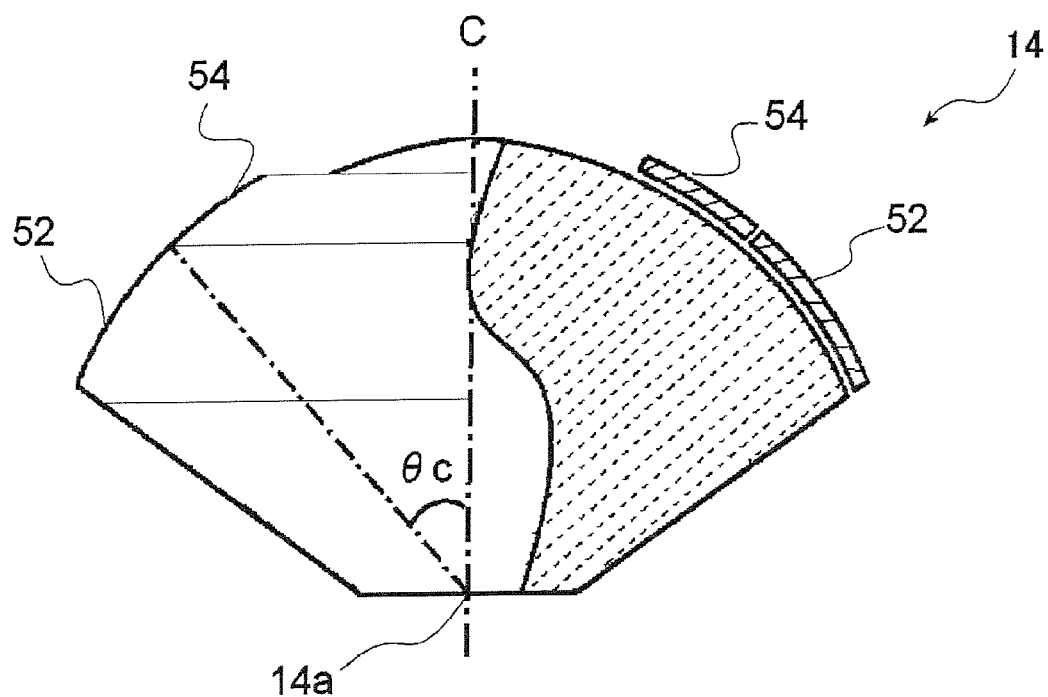
FIG. 2 is an illustration of a total reflection prism to which a filter is stuck, and which is a feature of the present invention.

The present invention is featured in that the acquisition of the total reflection spectra can be performed simultaneously with the visual observation of the measurement object. To this end, in the present embodiment, a visible light filter 52 and an infrared light filter 54 are provided on the hemispherical total reflection prism 14 as shown in a partial cross-sectional view of FIG. 2.

That is, the visible light filter 52 is configured to correspond to the total reflection area of the hemispherical total reflection prism 14, that is, the area in which the angle of the light beam incident on the prism bottom surface 14a becomes the critical angle $\theta_c$ or more, and thereby to remove the visible light beam. The visible light filter 52 is stuck in a strip form to the hemispherical surface of the prism 14.

Further, the infrared light filter 54 is configured to correspond to the normal reflection area of the prism 14, that is, the area in which the angle of the light beam incident on the prism bottom surface 14a is the critical angle or less, and thereby to remove the infrared light beam. The infrared light filter 54 is stuck in a strip form to the hemispherical surface of the prism 14.

Figure 3:
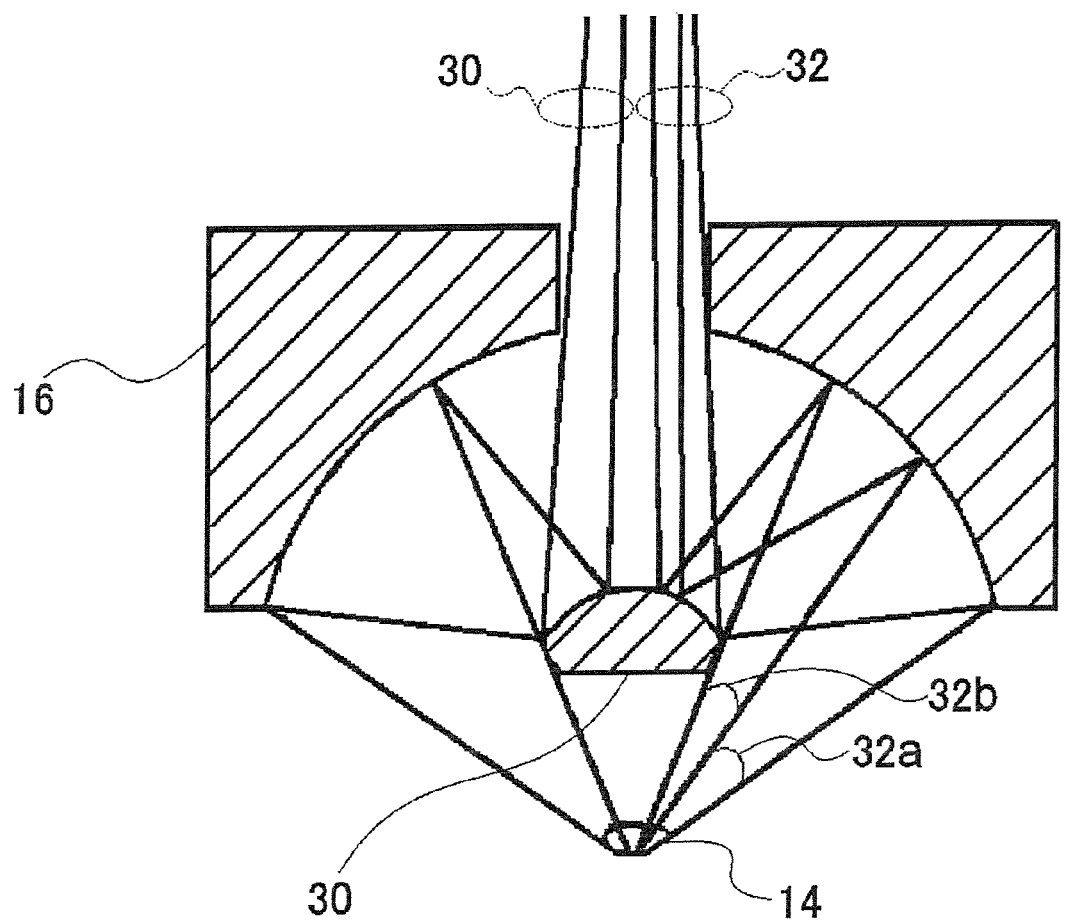
FIG. 3 is an illustration of a state where a normal reflection area and a total reflection area are formed in the total reflection prism shown in FIG. 2.

For this reason, as shown in FIG. 3, when the incident light beam 30 formed by mixing the visible light beam with the infrared interference light beam is made incident on the prism 14, only the infrared interference light beam 32a passes through the total reflection area, and only the visible light beam 32b passes through the nounal reflection area. Thus, the infrared interference light beam is irradiated onto the prism bottom surface 14a (boundary surface with the measurement object) at the critical angle $\theta_c$ or more, and is totally reflected by the boundary surface.

On the other hand, the visible light beam 32b having passed through the normal reflection area is irradiated onto the prism bottom surface 14a at the critical angle $\theta_c$ or less, and is normally reflected in the state where the observation information of the boundary surface between the prism bottom surface 14a and the measurement object is held.

Then, as described above, the reflected light beams are transmitted to the separation half mirror 38 via the Cassegrain primary mirror 16 and the Cassegrain secondary mirror 18, so that the light beams are separated into the visible light beam and the infrared interference light beam by the separation half mirror 38. The visible light beam is guided to the eyepiece 40 so as to be utilized for visual observation, while the infrared interference light beam is guided to the MCT detector 42 so as to be utilized for component analysis, and the like.

In this way, in the present invention, it is possible to directly visually observe the image of the area where the incident light beam is actually totally reflected. Particularly, in such a case where the measurement object 20 is pressed by the prism 14, the visual observation of the measurement object can be performed simultaneously with the collection of the spectra.

Further, the visual observation can be performed only by the normally reflected light beam, and hence the totally reflected visible light beam does not hinder the observation. Further, the solid angle of the optical path of the visible light beam is large, and hence the spatial resolution is high. Further, since the infrared light filter 54 is used in the present embodiment, only the totally reflected infrared interference light beam needs to be collected at the time of collection of the spectra. Thus, the visible light beam or the normally reflected infrared light beam does not affect the S/N ratio at the time of collection of the spectra.

Note that in the present embodiment, an example, in which the filter is provided on the prism surface, is described. However, the present embodiment may also be configured such that a concentric circular filter is provided on the optical path of the incident light beam or of the reflected light beam, so as to allow the visible light beam to pass through the normal reflection area and to allow the infrared interference light beam to pass through the total reflection area.

In the present embodiment, it is preferred that a material, such as diamond, ZnS (zinc sulfide), ZnSe (zinc selenide), and KRS-5 (thallium bromoiodide), having high transparency to the visible light and the infrared light is used for the prism.

Further, in the present embodiment, an optical material for visible light, such as quartz and BK7, may be used for the infrared light filter stuck to the prism surface, and an optical material, such as Ge and Si films, may be used for the visible light filter.

Further, the normally reflected light beam and the totally reflected light beam are spatially separated from each other in the reflected light beam, and the infrared light beam does not greatly affect the visual observation. Thus, the reflection mirror which guides only the reflected light beam in the normal reflection area to the eyepiece 40 may also be used as the visible light filter as well as the separation half mirror.

As described above, with the microscopic total reflection measuring apparatus according to the present invention, it is possible to perform the visual observation in the state where the measurement object and the prism are brought into contact with each other. Thus, it is possible to surely set the spectrum measurement position without being influenced by the deformation of the measurement object.

Further, the microscopic total reflection measuring apparatus according to the present invention has advantages that the mechanism is simplified because, unlike the conventional apparatus, it is not necessary to switch the optical path between the case of acquisition of the observation image and the case of acquisition of the spectra, and that the reproducibility of measurement is improved because, even in the case of a measurement object which is deformed or damaged by being brought into contact with the total reflection prism, the spectrum measurement can be performed while observing the state of the measurement object.

What is claimed is:

1. A microscopic total reflection measuring apparatus, comprising:
    a Cassegrain mirror comprising a Cassegrain primary mirror and a Cassegrain secondary mirror having coincident central axes,
    a total reflection prism arranged below the Cassegrain secondary mirror,
    a visible light filter, and
    a detector,
    wherein the Cassegrain secondary mirror is configured to reflect an incident light beam that includes both a visible light component and an infrared light component to the Cassegrain primary mirror,
    wherein the Cassegrain primary mirror is configured to reflect the incident light beam reflected by the Cassegrain secondary mirror through the total reflection prism to an object to be measured, and to reflect a reflected light beam from the object to be measured to the Cassegrain secondary mirror,
    wherein the visible light filter is arranged on the total reflection prism to remove the visible light component of the reflected light beam in a total reflection area where angles of reflection relative to the coincident central axes are greater than a critical angle but not in a normal reflection area where angles of reflection relative to the coincident central axes are less than the critical angle, and
    wherein the apparatus is configured to permit visual observation of the visible light component of the reflected light beam that passed through the normal reflection area at the same time as spectra information is being obtained by the detector from the infrared light component of the reflected light beam that passed through the total reflection area.

2. The microscopic total reflection measuring apparatus according to claim 1, wherein the total reflection prism is hemispherical and the visible light filter is arranged concentrically on the total reflection prism.

3. The microscopic total reflection measuring apparatus according to claim 1, wherein an infrared light filter is arranged on the total reflection prism to remove the infrared light component of the reflected light beam in the normal reflection area.

* * * * *